US006955842B1

(12) United States Patent
Koch et al.

(10) Patent No.: US 6,955,842 B1
(45) Date of Patent: Oct. 18, 2005

(54) SEALING MEDIUM FOR COMPOSITE PACKAGING MATERIALS

(75) Inventors: Reinhard Koch, Sinzig (DE); Frank Müller, Klaus/Vorarlberg (AT); Jorgen Friies, Odense (DK)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 09/308,407

(22) PCT Filed: Oct. 10, 1997

(86) PCT No.: PCT/EP97/05588

§ 371 (c)(1),
(2), (4) Date: Jul. 8, 1999

(87) PCT Pub. No.: WO98/23265

PCT Pub. Date: Jun. 4, 1998

(30) Foreign Application Priority Data

Nov. 29, 1996 (DE) ................ 196 49 534

(51) Int. Cl.7 ............. B29D 22/00; B29D 23/00; B32B 1/08
(52) U.S. Cl. ............ 428/35.4; 428/35.7; 428/36.6; 428/35.3; 428/35.8; 428/35.2; 428/36.7; 428/34.3; 206/484; 424/449
(58) Field of Search ............ 424/447, 449; 206/438, 440, 441, 484; 428/35.3, 35.8, 35.2, 428/35.7, 36.6, 36.7, 34.3, 35.4, 457, 500

(56) References Cited

U.S. PATENT DOCUMENTS

| | | | | |
|---|---|---|---|---|
| 3,938,659 A | * | 2/1976 | Wardell | 206/439 |
| 4,573,996 A | * | 3/1986 | Kwiatek et al. | 604/897 |
| 4,699,792 A | | 10/1987 | Nick et al. | 424/446 |
| 4,700,531 A | * | 10/1987 | Hsu et al. | 53/412 |
| 4,956,181 A | * | 9/1990 | Bayer et al. | 424/448 |
| 5,077,104 A | * | 12/1991 | Hunt et al. | 428/34.3 |
| 5,447,772 A | * | 9/1995 | Flieger | 428/99 |
| 5,449,552 A | | 9/1995 | Bochow et al. | 428/323 |
| 5,567,489 A | * | 10/1996 | Allen et al. | 428/34.1 |
| 5,698,217 A | * | 12/1997 | Wilking | 424/448 |
| 6,054,196 A | * | 4/2000 | Koch et al. | 428/34.3 |

FOREIGN PATENT DOCUMENTS

EP      0 563 507 A1    8/1992
WO    WO 94/04109    3/1994

* cited by examiner

Primary Examiner—Michael C. Miggins
(74) Attorney, Agent, or Firm—D. Peter Hochberg; Sean Mellino; Katherine R. Vieyra

(57) ABSTRACT

A sealing medium for composite packaging materials, in particular for packaging transdermal therapeutic systems (TTS) with volatile active ingredients such as nicotine, is characterized in that it is a heat sealing lacquer which is in the form of a liquid phase for application of extremely thin sealing layers in the printing process for example to partial areas of composite packaging materials.

12 Claims, 1 Drawing Sheet

SEALING MEDIUM FOR COMPOSITE PACKAGING MATERIALS

FIELD OF THE INVENTION

The invention relates to a sealing medium for composite packaging materials, in particular for packaging transdermal therapeutic systems (TTS) with active ingredients which are volatile in some cases.

BACKGROUND OF THE INVENTION

Sealing media for producing composite packaging materials of the type mentioned are known. They must be selected in respect of their properties so that they display, for example, no significant uptake of active ingredient from the TTS. Possible interactions with active substances or ancillary substances from the TTS must be strictly avoided or reduced as far as possible. In addition, the layer thicknesses of such media should be as small as possible because with large layer thicknesses there is observed to be in many cases an increased, unwanted interaction between product and packaging as a result of migration and penetration.

Comparatively thick layers of a sealing medium are also disadvantageous because the activation thereof in the brief melting process for bonding requires a comparatively large input of and time of exposure to heat for activating the sealing layer. To comply with these requirements, high-quality composite packaging materials have been used to date, and the sealing media employed therein have had to be applied in relatively large layer thicknesses between 20 and 60 microns with at least 20 g/m$^2$ because of the existing production processes. The said disadvantages arise from such large layer thicknesses.

SUMMARY OF THE INVENTION

The invention is based on the object of providing a sealing medium, with the use of which the abovementioned disadvantages and difficulties in the production of packs for active ingredient-containing plaster systems are avoided, which develops sufficiently high adhesive strengths when applied in an extremely thin layer, has the consistency of a printing ink which can be processed with conventional printing machines, allows insignificant uptake of active ingredient because of its chemical composition, in particular displays a barrier function towards volatile active ingredients such as nicotine, and can be used without difficulty in simple processes, for example without elaborate drying of a laminating adhesive or melting of a comparatively thick sealing film.

The object is achieved for a sealing medium of the type stated in the precharacterizing clause of claim 1 of the invention by providing a heat sealing lacquer which is in the form of a liquid phase for applying extremely thin sealing layers in a printing process for example to partial areas of composite packaging materials.

The achievement of the invention is that, as a consequence of its small layer thickness, the sealing lacquer permits insignificant uptake of active ingredient. Moreover the possibility of applying the sealing lacquer of the invention in a printing process partially to areas of packaging materials means a further reduction in the amount used and thus in the costs of materials as well as possible interactions with active ingredient in the packaged plaster. The small amount of sealing medium used has advantages both in ecological and in economic respects not only for the production of plaster packaging but also for the disposal thereof. In addition, application in a printing process facilitates accurate partial use of the sealing lacquer only in the sealing area and thus reduces interactions between product and packaging material. On the other hand, partial use of the sealing lacquer only in the sealing area means that it is possible to have packaging systems in which desired interactions, for example in the case of moisture absorbers, between product and packaging can take the desired form. By contrast, with the full-area sealing layers previously employed the films or sheets always formed a first layer completely surrounding the product of a packaging.

Further embodiments of the invention are provided as specified in the dependent claims. The result in these tests is an optimization in ecological and economic terms as a result of the small amount of sealing lacquer to be applied with the aid of conventional simple printing machines, and of the minimization of the raw materials, which are mostly very costly, used for these purposes, both for the production of the packaging materials and for the disposal thereof.

The invention makes it possible for sealing layers which can be applied thereby to packaging material areas to have weights per unit area between 1 and 15 g/m$^2$, preferably weights per unit area between 2.5 and 3.5 g/m$^2$.

In addition, one embodiment of the invention provides for the sealing medium to be or contain an ethylene/methacrylic acid copolymer dispersion and for it to result, by reason of its chemical composition, in no measurable uptake of active ingredient. By reason of its chemical composition, it has an advantageous barrier effect towards volatile active ingredients, in particular nicotine. It can furthermore be activated very advantageously, when present in the form of an extremely thin sealing layer, to form an adhesive melt phase with, by comparison, extremely small input of and time of exposure to heat. On the one hand, energy is saved, and, on the other hand, the production speed of available systems for producing different packaging materials and packs can be considerably increased, and thus the productivity can be significantly improved.

Finally, the invention achieves adhesion forces for the sealing medium, after activation and formation of an adhesive layer, which are in the region of the strength of the packaging materials which can be bonded therewith.

DETAILED DESCRIPTION OF THE INVENTION

Figure 1:
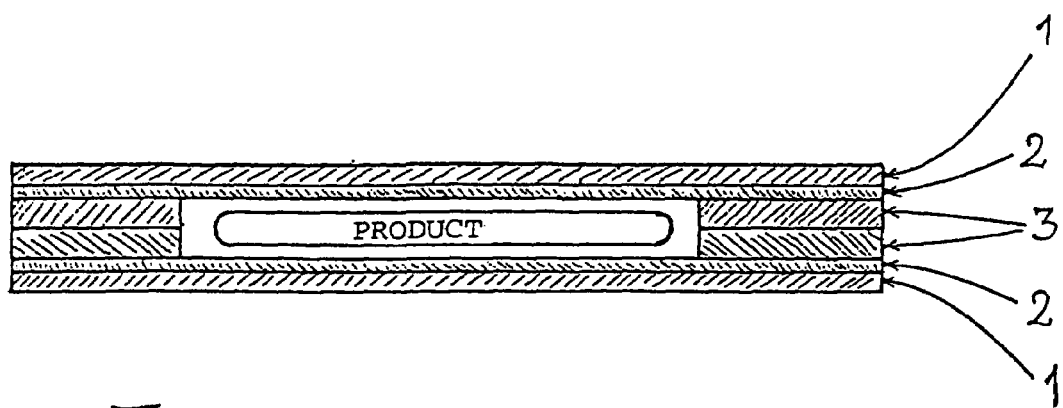
FIGS. 1 and 2 show packages produced with a sealing medium of the invention for active ingredient-containing TTS.

FIG. 1 shows a package with an upper and lower backing layer 1 and with an upper and lower barrier layer, for example an aluminium foil, and sealing lacquer layers 3 partially applied to the barrier layers 2.

Figure 2:
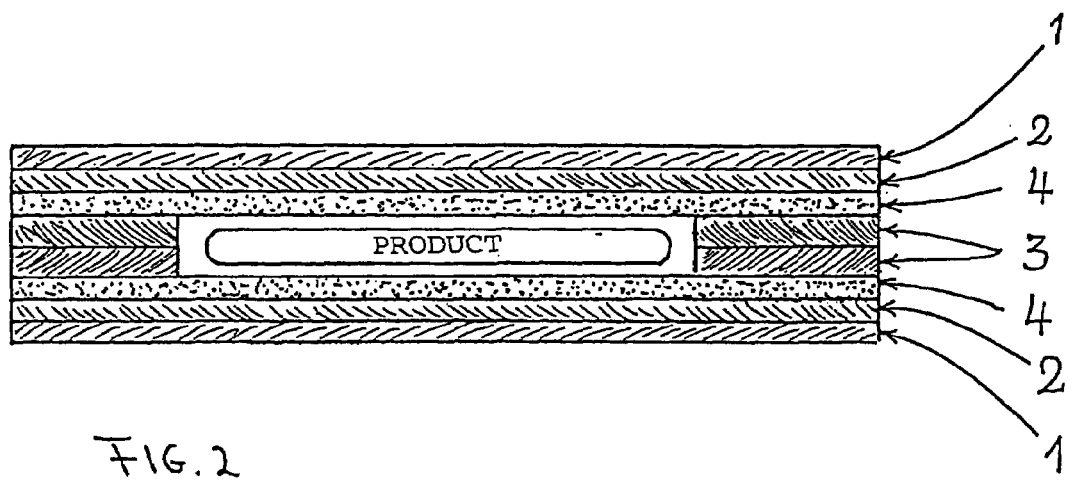

FIG. 2 shows a somewhat different embodiment of the package with an upper and lower backing layer 1, barrier layers 2, for example an aluminium foil, underneath which is a flat packaging element 4 which interacts with the product, for example a moisture absorber, and finally partially applied sealing lacquer layers 3.

The invention makes it possible, in both a particularly economical and a particularly ecological manner, both to produce and to dispose of specific packagings for TTS, in particular those with volatile active ingredients, and meets the object stated at the outset in an optimal manner.

What is claimed is:

1. A sealed packaging system composed of composite packaging material which contains a product having volatile active ingredients, said composite material having a strength and no significant uptake of active ingredients of the product, said packaging system comprising:
   layers defining a space for holding the product between said layers, said layers comprising
      barrier layers on opposite sides of the space holding the product forming a barrier against volatile active ingredients; and
      heat-sealing lacquer layer(s) between said respective opposite barrier layers, said heat-sealing lacquer layers:
         extending around the space for holding the product,
         being initially in a liquid phase applicable with printing machines;
         having no significant uptake of the active ingredient;
         having a weight per unit area in the range of between 1 and 15 grams per meter squared (g/m$^2$); and
         establishing adhesive forces after heat activation to form an adhesive layer having an adhesive strength in a region of strength of the packaging material
   wherein layers on both sides of the space for holding the product comprise opposing sealing area surfaces extending around the space for holding the product, said heat-sealing lacquer layers adhering to said sealing area surfaces.

2. A packaging system according to claim 1 wherein the heat sealing lacquer layers cover only the sealing area.

3. A packaging system according to claim 1 wherein said heat-sealing lacquer layer has a weight per unit area in the range of between 2.5 and 3.5 grams per meter squared (g/m$^2$).

4. The packaging system according to claim 1 wherein said heat-sealing lacquer layer comprises a heat-sealing medium composed of a ethylene/methacrylic acid copolymer dispersion having no measurable uptake of the active ingredient, when compared with a heat-sealing medium applied in a relatively thicker sealing layer.

5. The packaging system according to claim 1 wherein said barrier layers are composed of aluminum foil.

6. The packaging system according to claim 1 comprising backing layers disposed on opposite sides of said barrier layers distal from the space for holding the product.

7. The packaging system according to claim 1 wherein said opposing sealing surface areas are on the inner surface of said barrier layers adjacent the space for holding the product.

8. The packaging system according to claim 1 comprising flat packaging layers disposed inwardly from said barrier layers proximal the space for the product for interacting with the product.

9. The packaging system according to claim 8 wherein said flat packaging layers are moisture absorbers.

10. The packaging system according to claim 9 wherein said opposing sealing area surfaces are on the inner surfaces of said flat packaging layers adjacent the space for holding the product.

11. A packaging system according to claim 1 wherein the product is a transdermal therapeutic system.

12. A packaging system according to claim 11 wherein said barrier layers form a barrier against nicotine.

* * * * *